US006620425B1

(12) United States Patent
Gardiner

(10) Patent No.: US 6,620,425 B1
(45) Date of Patent: *Sep. 16, 2003

(54) FOOD SUPPLEMENTS AND METHODS COMPRISING LIPOIC ACID AND CREATINE

(75) Inventor: Paul T. Gardiner, Brampton (CA)

(73) Assignee: Muscletech Research and Development Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/666,432

(22) Filed: Sep. 21, 2000

Related U.S. Application Data

(63) Continuation of application No. 09/138,136, filed on Aug. 21, 1998, now Pat. No. 6,136,339.

(51) Int. Cl.$^7$ .................... A61K 31/385; A61K 31/195; A61K 47/00
(52) U.S. Cl. ................. 424/439; 514/561; 514/440
(58) Field of Search ................ 424/439; 514/561, 514/440

(56) References Cited

U.S. PATENT DOCUMENTS

| | | | |
|---|---|---|---|
| 4,070,488 A | * | 1/1978 | Davis |
| 4,446,231 A | | 5/1984 | Self |
| 4,598,042 A | | 7/1986 | Self |
| 4,687,782 A | * | 8/1987 | Brantman |
| 4,766,004 A | | 8/1988 | Moskowitz |
| 4,769,321 A | | 9/1988 | Self |
| 4,976,960 A | * | 12/1990 | Grossman et al. |
| 5,026,721 A | * | 6/1991 | Dudrick et al. |
| 5,032,506 A | | 7/1991 | Palmer et al. |
| 5,051,258 A | | 9/1991 | Sahley |
| 5,084,481 A | | 1/1992 | Ulrich et al. |
| 5,143,842 A | | 9/1992 | Ham et al. |
| 5,164,384 A | * | 11/1992 | Paul |
| 5,227,307 A | | 7/1993 | Bar-Or et al. |
| 5,290,519 A | | 3/1994 | Bar-Or et al. |
| 5,324,656 A | | 6/1994 | Ham et al. |
| 5,334,612 A | | 8/1994 | Kalden et al. |
| 5,470,838 A | | 11/1995 | von Borstel et al. |
| 5,569,670 A | | 10/1996 | Weischer et al. |
| 5,583,117 A | | 12/1996 | von Borstel et al. |
| 5,691,320 A | | 11/1997 | von Borstel et al. |
| 5,691,379 A | | 11/1997 | Ulrich et al. |
| 5,725,804 A | | 3/1998 | Yen |
| 5,728,735 A | | 3/1998 | Ulrich et al. |
| 5,736,531 A | | 4/1998 | von Borstel et al. |
| 5,756,291 A | | 5/1998 | Griffin et al. |
| 5,783,382 A | | 7/1998 | Aoyama et al. |
| 5,830,680 A | | 11/1998 | Meyerhoff et al. |
| 5,834,513 A | | 11/1998 | Ptchelintsev et al. |
| 5,847,003 A | | 12/1998 | Ptchelintsev et al. |
| 5,886,040 A | * | 3/1999 | Fang |
| 5,888,553 A | * | 3/1999 | Grant et al. |
| 5,925,378 A | * | 7/1999 | Carnazzo |
| 5,932,229 A | | 8/1999 | Ptchelintsev et al. |
| 5,951,990 A | | 9/1999 | Ptchelintsev |
| 5,968,914 A | | 10/1999 | von Borstel et al. |
| 5,976,568 A | | 11/1999 | Riley .................. 424/451 |
| 6,136,339 A | * | 10/2000 | Gardiner |

OTHER PUBLICATIONS

James, Wesley, "Lipoic Acid, the Undiscovered Wonder", *Muscle Maker Journal*, Nov. 1996, vol. 1, Issue 2.*

Netrition.com "Met–Rx Creatine AC" Online! Available from Internet: <URL:HTTP://www.Netrition.com/cyopro_page.HTML>, Nov. 30, 1999, pp. 1–7 XP002124392 p. 5.

Maximuscle "The Ultimate 'All In One' Power Product" Online! Available From Internet:<URL:www.maximuscle.com/cyclone.HTML> Jan. 12, 1999, XP00212446.

The Nutrasense Company "Creatine MTS Transport System", Online! Available From Internat:<URL: www.nutrasense.com/Nutrasense/CreatinEMTS.HTNL> Nov. 30, 1999, XP002124393.

Vitanet "Muscle Tech's Cell–Tech" Online! Available From Internet: <URL:HTTP://Store.Yahoo.com/Vitanet/Musteccel 4P0.HTML> Nov. 30, 1999, XP002124394.

Physically Enhancement "Extreme Supplementation" Online! Available For Internet: <URL:HTTP://Physicalenhancement.com/supp/extreme4.HTML> Nov. 30, 1999, XP002124395.

Vandenberghe et al, *Journal of Applied Physiology*, 83(6):2055–2063 (1997).

Green et al, *American Journal of Physiology*, 271 (5 pt 1):E821–E826 (1996).

Jacob et al, *Diabetes*, 45(8):1024–1029 (1996).

Streeper et al, *American Journal of Physiology*, 273 (1 Pt 1):E185–E191 (1997).

Estrada et al, *Diabetes*, 45(12):1798–1804 (1996).

Jacob et al, *Arzeinmittelforschung*, 45(8):872–4 (1995).

Roy et al, *Biochemical Pharmacology*, 53(3):393–399 (1997).

Anan, *Equine Veterinary Data*, 13:319 (1992).

Birch et al, *European Journal of Applied Physiology*, 69:268–270 (1994).

Dawson et al, *The Australian Journal of Science and Medicine in Sport*, 27(3):56–61 (1995).

Harris et al, *Journal of Physiology*, 467:74P (1993).

Khamaisi et al, *Metabolism*, 46(7):763–768 (1997).

Biewenga, *General Pharmacology*, 29(3):315–331 (1997).

Greenhaff, *Muscle Media 2000*, pp. 98–102 (undated).

Bummer, *IM*, pp. 56–60 (1996).

Weider Research Group, *Muscle & Fitness*, pp. 146–148 (Feb. 1998).

(List continued on next page.)

*Primary Examiner*—Thurman K. Page
*Assistant Examiner*—Amy E Pulliam
(74) *Attorney, Agent, or Firm*—Kenyon & Kenyon

(57) ABSTRACT

Food supplement compositions comprise lipoic acid or a derivative thereof and creatine or a derivative thereof. The compositions optionally, but preferably, further comprise dextrose. The food supplement compositions are suitable for supplementing the diet of an athlete and particularly for enhancing an athlete's muscle size or strength.

18 Claims, No Drawings

OTHER PUBLICATIONS

Murray, *Encyclopedia of Nutritional Supplements, Prima Publications*, pp. 343–346 (1996).
Brink et al, *Muscle & Fitness*, pp. 78–80, 214–215 (Jun. 1998).
Sanders, *University of California, Public Information Office Notice*, File #14316 (1996).
Anderson, *Regulatory Toxicology and Pharmacology*, 26(1 Pt 2):S35–S41 (1997).
Lefavi et al, *International Journal of Sport Nutrition*, 2(2):111–122 (1992).
Anderson et al, *Metabolism*, 32(9):894–899 (1983).
Vincent, *Journal of Nutrition*, 124(1):117–119 (1994).
Mertz, *Journal of Nutrition*, 123(4):626–633 (1993).
Mirsky, *Journal of Inorganic Biochemistry*, 49(2):123–128 (1993).
Kaats et al, *Current Therapeutic Research*, 57(10):747–756 (1996).
Bulbulian, *Medical Science of Sports and Exercise*, 28(Suppl.):S111 (1996).
Phillips, *Sport Supplemental Review, Mills High Publishing*, 3rd Issue, pp. 125, 173 (1996).
Volek et al, *Strength & Cond.*, 10(3):200–210 (1996).
Ferro, *Creatine & Athletic Performance*, http://www.seriousfun.net/weightlifting/creatine.htm (1998).
Burkart et al, *International Journal of Immunopharmacology*, 16:61 (1994).
Sachse et al, *Hormone Metabolism Research Supplement*, 9:105 (1980).
Ditre et al, *SDFC Reports*, Feb. 19, 1996.
Colgan, *Colgan Chronicles*, vol. 1, pp. 1, 3 (1997).
Dehaan, *MuscleMag International*, pp. 88–92 (1998).
Editorials, *MuscleMag International*, p. 48 (Jan. 1998).
Editorials, *MuscleMag International*, pp. 39–40 (Feb. 1998).
Editorials, *MuscleMag International*, p. 34 (Mar. 1998).
Editorials, *MuscleMag International*, p. 48 (Apr. 1998).
Editorials, *MuscleMag International*, p. 41 (Jun. 1998).
Editorials, *MuscleMag International*, pp. 37–38 (Jul. 1998).
Editorials, *MuscleMag International*, p. 52 (Dec. 1997).
Brewer, *MuscleMag International*, pp. 64–66, 68, 70, 72–73 (Jun. 1998).
Williams, *All Natural Muscular Development*, pp. 128–131, 218 (Nov. 1997).
Simmons, *MuscleMag International*, pp. 56–58, 60, 62–63 (Sep. 1998).
Editorial, *MuscleMag International*, pp. 128–131 (Jul. 1998).
Simmons, *MuscleMag International*, pp. 88–91 (Apr. 1998).
Lefebre, *MuscleMag International*, pp. 76–78, 80, 82–83 (Aug. 1998).
Editorial, *MuscleMag International*, pp. 102–104, 106, 108 (May 1998).
Editorials, *MuscleMag International*, pp. 35–36 (May 1998).
Editorial, *MuscleMag International*, pp. 52–53 (Nov. 1997).
Editorial, *MuscleMag International*, p. 53 (Nov. 1997).
Editorial, *MuscleMag International*, p. 53 (Dec. 1997).
Editorial, *MuscleMag International*, p. 46 (Aug. 1998).
Editorial, *MuscleMag International*, p. 36 (Sep. 1998).
Anderson, *Nutrition Reviews*, 56(9):266–270 (1998).
Jequier, *American Journal of Clinical Nutrition*, 1998:67(Suppl):527S–530S (1998).
Williams et al, *Journal of the American College of Nutrition*, 17(3):216–234 (1998).
Faust et al, *International Journal of Immunopharmacology*, 16(1):61–66 (1994).
Packer et al, *Free Radical Biology and Medicine*, 19(2):227–250 (1995).

\* cited by examiner

FOOD SUPPLEMENTS AND METHODS COMPRISING LIPOIC ACID AND CREATINE

CROSS-REFERENCE TO RELATED APPLICATIONS

This application is a continuation of application Ser. No. 09/138,136 filed Aug. 21, 1998, now U.S. Pat. No. 6,136,339 which is incorporated herein by reference.

FIELD OF THE INVENTION

The present invention is directed to food supplements which comprise lipoic acid or derivative thereof and creatine or a derivative thereof, and to methods for supplementing the diet of an athlete and methods for enhancing an athlete's muscle size or strength, which methods employ these food supplements.

BACKGROUND OF THE INVENTION

Creatine (also known as N-methyl-N-guanyl glycine or (alpha methyl guanido) acetic acid) is an amino acid compound produced naturally in the liver and kidneys and obtained from food such as meat and fish. Food supplements containing creatine, typically creatine monohydrate, are commonly used by athletes to allow them to train harder and enhance muscle size and strength. Various commercial products containing creatine monohydrate are available.

Lipoic acid (also known as alpha-lipoic acid, thioctic acid or 6,8-dithio octanoic acid) is a nutrient that the human body makes in minute quantities and may be obtained from yeast and liver. Studies have shown that lipoic acid can significantly increase the body's utilization of blood sugar in type II diabetics and that lipoic acid may increase the metabolic clearance rate of glucose by 50% in diabetics. In Europe, lipoic acid has been used as a substitute for insulin in the treatment of Type II diabetes.

Food supplements for enhancing an athlete's muscle size and strength have become popular substitutes for steroids and other drugs in various sports and body building regimes. However, as athletes continually strive for improved performance, there is a continuing need for non-steroid containing aids for improving muscle size and strength.

SUMMARY OF THE INVENTION

Accordingly, it is an object of the present invention to provide new food supplements. It is a more specific object of the invention to provide food supplements particularly adapted for supplementing the diet of an athlete. It is another object to provide food supplements which may enhance an athlete's muscle size or strength. It is a further object of the invention to provide non-steroid containing food supplements and to provide food supplements which may be conveniently administered to the diet of an athlete.

These and additional objects are provided by the food supplements and methods according to the present invention. The food supplements comprise lipoic acid or a derivative thereof, for example a salt or ester thereof, and creatine or a derivative thereof, for example a hydrate, salt or ester thereof. The food supplements may optionally, and preferably, further comprise dextrose. It has been determined that such food supplement compositions are advantageous for supplementing the diet of an athlete and may provide surprising enhancement of an athlete's muscle size or strength when administered to an athlete's diet. These and additional objects and advantages will be more fully apparent in view of the following detailed description.

DETAILED DESCRIPTION

The food supplement compositions of the present invention comprise lipoic acid or a derivative thereof and creatine or a derivative thereof. Creatine and hydrates thereof, particularly creatine monohydrate, are known to improve and/or enhance muscle size and/or strength. The food supplements and methods of the present invention may provide further and significant muscle size and strength enhancement or improvement as compared with supplements and methods employing only creatine or a hydrate thereof. Although the present invention is not to be limited by any theoretical explanation, it is believed that insulin is a primary factor that stimulates glucose and creatine transport into the muscle cells and that the lipoic acid both mimics and enhances the actions of insulin in glucose and creatine transport into the muscle cells. In preferred embodiments, the compositions further include dextrose which has been shown to stimulate insulin action.

The food supplements comprise lipoic acid or a derivative thereof, for example a salt or ester thereof. Suitable salts include, but are not limited to, alkali and alkaline earth metal salts, for example sodium, potassium or calcium salts, while suitable esters include, but are not limited to, alkyl esters, for example, methyl, ethyl or propyl esters, or lactone esters.

The food supplement compositions further comprise creatine or a derivative thereof, for example a hydrate, salt or ester thereof. Commercially available creatine derivatives include creatine monohydrate, other creatine hydrates, creatine citrate and creatine pyruvate. The creatine which is employed in the food supplement compositions of the present invention preferably comprises creatine monohydrate, commercially available from various sources. It is similarly preferred that the creatine, creatine monohydrate or other creatine derivative is a pharmaceutical-grade material. As set forth above, the food supplement compositions also preferably further comprise dextrose (glucose), with pharmaceutical-grade dextrose being preferred.

The food supplement compositions of the present invention may be provided in liquid or powder form, with powders suitable for mixing with water or other liquids being preferred. The food supplement compositions in powder or granular form may be provided in accordance with customary processing techniques, for example as spray dried powders, or the like. Owing to the lipoic acid component, the food supplement compositions generally exhibit an acidic pH value.

The lipoic acid or salt, ester or other derivative thereof is employed in the food supplement compositions according to the present invention in an amount sufficient to increase creatine transport into the muscle cells. In a preferred embodiment, the food supplement compositions comprise from about 0.1 mg to about 10 mg lipoic acid or derivative thereof per gram of supplement and from about 0.01 g to about 0.5 g of creatine, preferably creatine monohydrate, or derivative thereof, per gram of supplement. In further preferred embodiments, the food supplement compositions comprise from about 0.5 mg to about 5 mg lipoic acid derivative thereof per gram of supplement and from about 0.05 g to about 0.25 g of creatine or derivative thereof per gram of supplement. Even more preferably the food supplement compositions comprise from about 1 mg to about 3 mg lipoic acid, salt, ester or other derivative thereof per gram of supplement and from about 0.05 g to about 0.2 g of creatine, creatine monohydrate or other derivative thereof per gram of supplement. Food supplement compositions further comprising dextrose preferably include the dextrose in an amount sufficient to stimulate insulin secretion and preferably the food supplement compositions comprise from about 0.1 g to about 0.9 g dextrose per gram of supplement. In further preferred embodiments, the food supplement compositions comprise from about 0.4 g to about 0.9 g dextrose per gram of supplement, and more preferably comprise from about 0.5 g to about 0.8 g dextrose per gram of supplement. Most preferably, the food supplement compositions comprise about 0.75 g dextrose per gram of supplement.

The food supplement compositions according to the present invention may further contain additional components to further increase the speed at or ease with which creatine enters the bloodstream and subsequently the muscle tissue, or to otherwise enhance the effects of the creatine in the body. For example, additional amino acids may be included in the food supplement compositions. Suitable amino acids include, but are not limited to, glutamine, alanine, taurine, carnitine, acetyl-L-carnitine, and the like. These additional amino acids may stimulate cell volumization and protein synthesis and therefore provide further advantages to increasing muscle strength and/or size. These amino acids may be employed individually or in various combinations and in amounts customary in the art, for example in the range of from about 0.01 mg to about 100 mg per gram of food supplement.

In a further preferred embodiment, the food supplement compositions also include a chromium compound. Again, while not intending to be limited by theory, various studies have indicated that chromium supplementing will improve glucose tolerance in insulin-sensitive individuals by up to 50% and thereby maximize insulin efficiency. Chromium is a constituent of a biologically active compound, the glucose tolerance factor (GTF), found in foods such as organ meats, whole grains, cheese, mushrooms and brewer's yeast. Various chromium compounds may be included in the food supplement compositions, and in amounts effective to improve insulin efficiency. A preferred chromium compound is chromium picolinate, which may be included, for example in an amount of from about 50 to about 500 micrograms per 100 grams of supplement. Additional components for the food supplement compositions include additional minerals such as magnesium, potassium, phosphorous, salts thereof, or mixtures thereof in amounts conventional in the art, for example, from about 0.01 mg to about 100 mg per gram of food supplement. The food supplement compositions also preferably contain ascorbic acid (vitamin C), for example in amounts equal to or exceeding the recommended minimum daily requirements. Another component for use in the food supplements comprises beta-hydroxy, beta-methyl butyrate (HMB), in amounts known in the art.

The food supplement compositions may further comprise natural and/or artificial flavoring components, dyes or other coloring additives, preservatives and other conventional food supplement additives known in the art.

The food supplements according to the present invention may be employed in methods for supplementing the diet of an athlete, and/or for enhancing an athlete's muscle size or strength. The food supplement compositions of the present invention are particularly advantageous for creating an increased anabolic environment and obtaining extra growth in lean muscle mass and strength. The amount of the food supplement composition which is administered to the diet of the athlete may vary depending on the desired effect, the body weight and characteristics of the athlete, and the like. For example, in preferred methods for supplementing the diet of an athlete and/or for enhancing an athlete's muscle size or strength, from about 10 mg to about 1,000 mg of lipoic acid, salt, ester or other derivative thereof and from about 1 g to about 50 g of creatine, creatine monohydrate, or other derivative thereof are administered to the diet of the athlete on a daily basis. In more preferred embodiments of these methods, from about 50 mg to about 500 mg of lipoic acid or derivative thereof and from about 5 g to about 25 g of creatine, creatine monohydrate or other derivative thereof are administered to the diet of the athlete on a daily basis. The food supplement may be administered in a single serving or in multiple servings spaced throughout the day. In alternate preferred embodiments, from about 100 mg to about 300 mg of lipoic acid or derivative thereof and from about 5 g to about 20 g of creatine, creatine monohydrate or other derivative thereof are administered to the diet of the athlete on a daily basis.

To facilitate such administration, preferred embodiments of the food supplement of the invention comprise from about 0.1 mg to about 10 mg lipoic acid or derivative thereof per gram of supplement and from about 0.01 g to about 0.5 g of creatine, creatine monohydrate, or other derivative thereof per gram of supplement, and the supplement is administered in an amount of from about 10 g to about 500 g per day. In additional embodiments, such supplements are administered in an amount of from about 50 g to about 300 g per day, in one or multiple servings throughout the day.

In additional embodiments wherein the supplement further comprises dextrose, from about 10 mg to about 1,000 mg of lipoic acid or derivative thereof, from about 1 g to about 50 g of creatine, creatine monohydrate or other derivative thereof, and from about 10 g to about 300 g of dextrose are administered to the diet of the athlete on a daily basis. In further preferred embodiments, from about 50 mg to about 500 mg of lipoic acid or derivative thereof, from about 5 g to about 25 g of creatine, creatine monohydrate, or other derivative thereof, and from about 50 g to about 200 g of dextrose administered to the diet of the athlete on a daily basis. Most preferably, each supplement serving comprises from about 100 mg to about 300 mg lipoic acid or a derivative thereof, from about 5 g to about 20 g of creatine, creatine monohydrate or other derivative thereof, and from about 50 g to about 90 g, more preferably about 75 g, of dextrose.

When the food supplement further comprises dextrose, a supplement comprising from about 0.1 mg to about 10 mg lipoic acid or derivative thereof per gram of supplement, from about 0.01 g to about 0.5 g of creatine or derivative thereof per gram of supplement, and from about 0.1 g to about 0.9 g dextrose per gram of supplement, preferably from about 0.5 g to about 0.8 g dextrose per gram of supplement, may be administered in an amount of from about 10 g to about 500 g, more preferably from about 50 g to about 300 g, per day.

In one embodiment of the methods according to the present invention, increased servings of the food supplement according to the present invention may be initially administered to the athlete's diet in order to increase or enhance the athlete's muscle size or strength, followed by a maintenance period in which decreased servings of the food supplement may be administered. The initial period may be at least several days and may extend up to several weeks as desired. Once a desired muscle strength and/or size has been obtained, lower servings of the food supplement may be administered to the athlete's diet in order to maintain the increased muscle size and/or strength. These features will be discussed in further detail in the examples. Additionally, in order to maximize the effects of the food supplement in enhancing muscle size and/or strength, it is preferred that the food supplement is administered to the diet of the athlete immediately following an exercise period. On non-workout days, the food supplement may be administered anytime during the day, although administering the food supplement upon awakening or otherwise during the morning hours is preferred.

The food supplement compositions and methods of the invention are further illustrated in the following examples. In the examples and throughout the present specification, parts and percentages are by weight unless otherwise specified.

EXAMPLE 1

In this example, an athlete consumes two servings of the food supplement as described herein daily, one in the morning and the other twelve hours later or immediately after his/her exercise workout. This regime is continued for five days in order to enhance muscle size and/or strength. Each serving of the food supplement is approximately 100 g and contains the following:

| Component | Amount |
| --- | --- |
| Lipoic Acid | 200 mg |
| Creatine Monohydrate | 10 g |
| Dextrose | 75 g |
| Taurine | 2000 mg |
| Vitamin C | 250 mg |
| Magnesium | 70 mg |
| Potassium | 150 mg |
| Phosphorous | 100 mg |
| Chromium Picolinate | 300 mcg |

Each approximate 100 gram serving is mixed with 12 ounces of cold water to provide a liquid drink. An additional 8 ounces of water is consumed after the food supplement liquid drink is consumed.

EXAMPLE 2

The muscle size and/or strength enhancing regime of Example 1 is modified so that the athlete consumes four servings of the food supplement daily, with each serving being approximately 50 g of the supplement and comprising:

| Component | Amount |
| --- | --- |
| Lipoic Acid | 100 mg |
| Creatine Monohydrate | 5 g |
| Dextrose | 37.5 g |
| Taurine | 1000 mg |
| Vitamin C | 125 mg |
| Magnesium | 35 mg |
| Potassium | 75 mg |
| Phosphorous | 50 mg |
| Chromium Picolinate | 150 mcg |

Each supplement serving is mixed with 12 ounces of cold water and the servings are administered at approximately evenly spaced times through the day, with one serving being consumed immediately after the athlete's exercise workout.

EXAMPLE 3

Once the regime described in Example 1 is completed, the athlete continues with a maintenance regime wherein one serving of the food supplement composition described in Example 1 is consumed on a daily basis. The serving is consumed immediately after an exercise workout or, on non-workout days, upon awakening or otherwise in the morning hours. As described in Example 1, the approximate 100 gram serving is mixed with cold water to form a liquid drink. Alternatively, the food supplement is be combined with other liquid drinks or foods as desired. This maintenance regime is continued for at least eight weeks to maintain enhanced muscle size and/or strength.

The servings set forth in these examples are designed for a 2000 calorie diet. Daily values may be increased or decreased depending on the calorie needs of individual athletes, and/or body weights of individual athletes.

The examples and embodiments set forth in the present application are provided only to illustrate various aspects of the invention and additional embodiments and advantages of the food supplements and methods of the present invention will be apparent to those skilled in the art.

What is claimed is:

1. A food supplement, comprising lipoic acid or a derivative thereof and creatine or a derivative thereof, wherein the creatine is selected from the group consisting of creatine hydrates.

2. A food supplement, comprising lipoic acid or a derivative thereof and creatine or a derivative thereof, wherein the creatine is creatine citrate.

3. A food supplement, comprising lipoic acid or a derivative thereof and creatine or a derivative thereof, wherein the creatine is creatine pyruvate.

4. A food supplement, comprising lipoic acid or a derivative thereof and a creatine or a derivative thereof, further comprising magnesium, potassium, phosphorous, salts or mixtures thereof.

5. The food supplement of claim 4, wherein the mixture is about 0.01 mg to about 100 mg per gram of food supplement.

6. A food supplement, comprising lipoic acid or a derivative thereof and creating or a derivative thereof, further comprising ascorbic acid in amounts equal to or exceeding the recommended minimum daily requirements.

7. A food supplement, comprising lipoic acid 200 mg, creatine monohydrate 10 g, dextrose 75 g, taurine 2000 mg, vitamin C 250 mg, magnesium 70 mg, potassium 150 mg, phosphorous,100 mg, and chromium picolinate 300 mcg.

8. A food supplement, comprising lipoic acid 100 mg, creatine monohydrate 5 g, dextrose 37.5 g, taurine 1000 mg, vitamin C 125 mg, magnesium 35 mg, potassium 75 mg, phosphorous 150 mg, and chromium picolinate 50 mcg.

9. A method for supplementing the diet of an athlete, comprising administering to the diet of the athlete the food supplement of claim 1.

10. A method for supplementing the diet of an athlete, comprising administering to the diet of the athlete the food supplement of claim 2.

11. A method for supplementing the diet of an athlete, comprising administering to the diet of the athlete the food supplement of claim 3.

12. A method for supplementing the diet of an athlete, comprising administering to the diet of the athlete the supplement of claim 4.

13. A method for supplementing the diet of an athlete, comprising administering to the diet of the athlete the supplement of claim 5.

14. A method for supplementing the diet of an athlete, comprising administering to the diet of the athlete the supplement of claim 7.

15. A method for supplementing the diet of an athlete, comprising administering to the diet of the athlete the supplement of claim 8.

16. A method for supplementing the diet of an athlete, comprising administering to the diet of the athlete the supplement of claim 7.

17. The method as in any on of the claims 9–16, wherein the food supplement is administered immediately following an exercise period.

18. A method of preparing a food supplement as in any one of claims 1–8, comprising the steps of preparing the lipoic acid and creatine in powder or liquid form.

* * * * *